United States Patent [19]

Deininger et al.

[11] Patent Number: 4,869,714
[45] Date of Patent: Sep. 26, 1989

[54] LUMINAL SURFACE FABRICATION FOR CARDIOVASCULAR PROSTHESES

[75] Inventors: William D. Deininger, Pasadena; Stephen B. Gabriel, La Crescenta, both of Calif.

[73] Assignee: California Institute of Technology, Pasadena, Calif.

[21] Appl. No.: 167,030

[22] Filed: Mar. 11, 1988

Related U.S. Application Data

[62] Division of Ser. No. 829,278, Feb. 13, 1986, Pat. No. 4,767,418.

[51] Int. Cl.⁴ .................. A61F 2/04; C23C 14/00; B44C 1/22; B29C 37/00
[52] U.S. Cl. ........................................ 600/36; 623/66; 156/643; 156/659.1; 156/668; 204/192.34; 204/192.35; 204/192.36
[58] Field of Search ............... 156/643, 659.1, 668; 204/192.34, 192.36, 192.35; 623/1, 12, 66; 600/36

[56] References Cited

U.S. PATENT DOCUMENTS 4,064,030 12/1977 Nakai et al. ............. 204/192.34 X
4,114,983 9/1978 Maffitt et al. ............ 204/192.32 X
4,325,998 4/1982 Chapman ....................... 156/668 X
4,502,916 3/1985 Umezaki et al. .......... 204/192.34 X
4,614,706 9/1986 Matsuzawa et al. ............ 156/643 X

FOREIGN PATENT DOCUMENTS 2036627 7/1980 United Kingdom ........... 204/192.35

Primary Examiner—Alan W. Cannon
Attorney, Agent, or Firm—Freilich Hornbaker Rosen & Fernandez

[57] ABSTRACT

A method is provided for forming a mold surface with microscopic upstanding pillars for molding the inside surface of a vascular prostheses (synthetic blood vessel). The mold article is formed from a quantity of Teflon (polytetrafluoroethylene) which has a polished, flat surface on which a gold film has been sputter deposited. A photoresist layer, which cannot adhere directly to Teflon, adheres to the gold. The photoresist is exposed and developed leaving a sputter resistant mask defining the desired pillar locations, and the resulting workpiece is ion etched to form the pillars in the Teflon. A synthetic blood vessel material is cast against the Teflon mold to form blind recesses on the inside of the synthetic blood vessel, with the recesses being of predetermined uniform cross section and present in a predetermined uniform pattern.

9 Claims, 2 Drawing Sheets

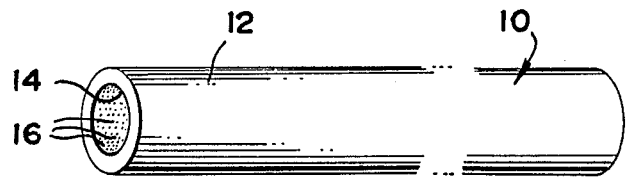
FIG. 1
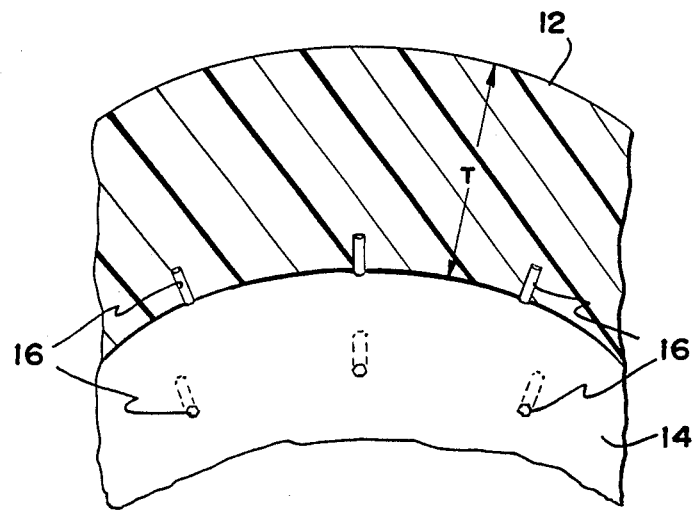
FIG. 2
FIG. 3
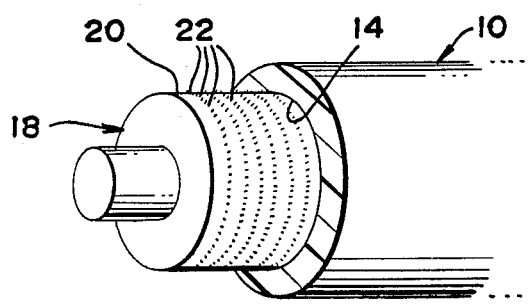
FIG. 4
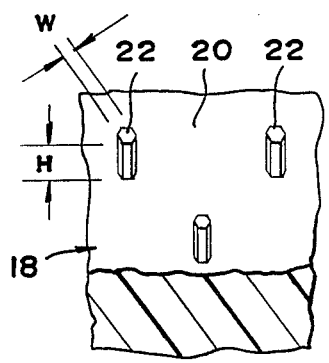
FIG. 5
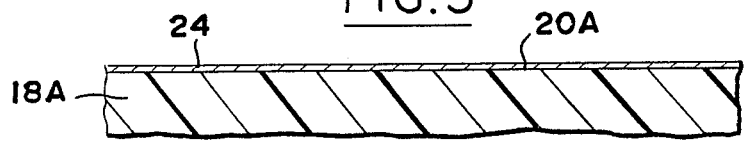

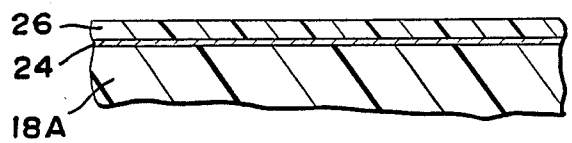
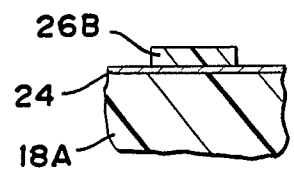
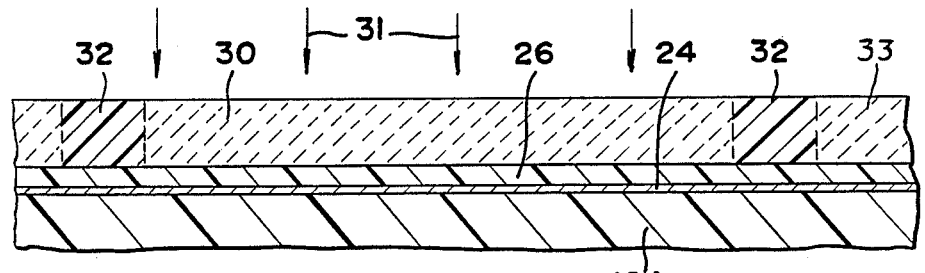
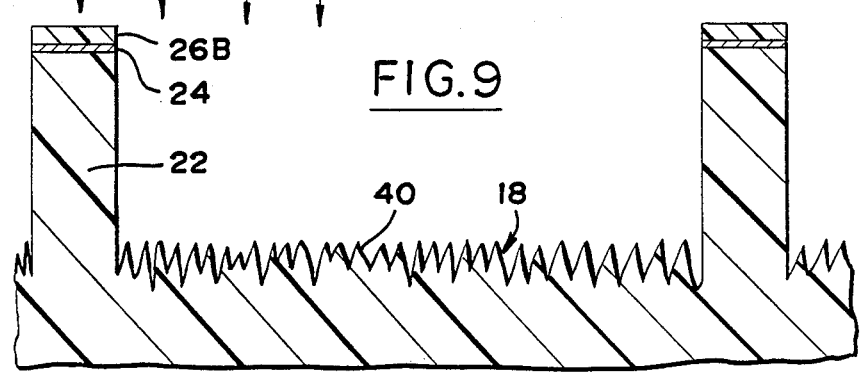
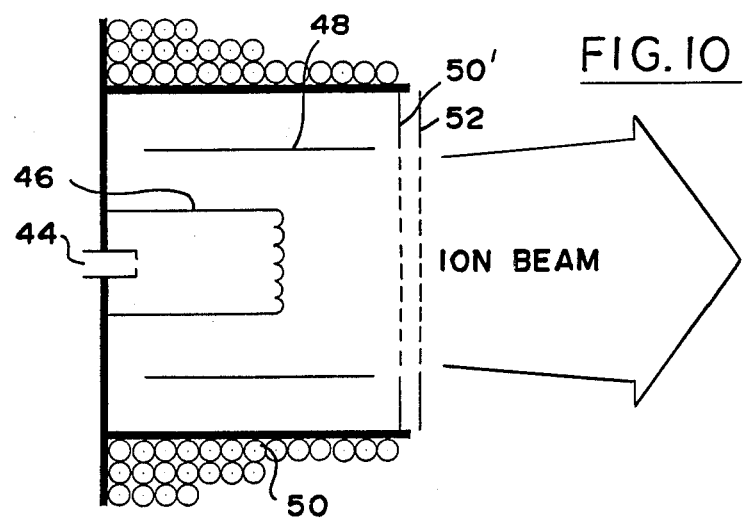

LUMINAL SURFACE FABRICATION FOR CARDIOVASCULAR PROSTHESES

ORIGIN OF INVENTION

This is a division of application Ser. No. 829,278, filed Feb. 13, 1986, now U.S. Pat. No. 4,767,418.

The invention described herein was made in the performance of work under a NASA contract and is subject to the provisions of Section 305 of the National Aeronautics and Space Act of 1958 Public Law 85-568 (72 Stat. 435; USC 2457).

BACKGROUND OF THE INVENTION

More than 250,000 vascular replacement devices are implanted every year in the United States alone. Most vascular prostheses are used to replace large internal diameter (over 6mm) blood vessels such as in the aorta and major arteries, and currently available replacements are generally considered satisfactory. However, small internal diameter (less than 6mm) vascular prostheses, such as those used for coronary arteries and peripheral vessels, suffer from low patency rates (they tend to be blocked). Recent efforts to develop suitable small diameter vascular prostheses have been hampered by an inability to find a material which promotes the development of a healthy neointima lining. If a proper surface is provided, such a lining is formed by the adsorption of proteins in the blood onto the surface followed by platelet and leukocyte adherence and fibrin polymerization, resulting in growth of a surface layer which includes a layer of endothelial cells in direct contact with the blood. If the luminal lining overdevelops, thrombus (bloodclots) can occur. If the lining does not adhere well to the inner surface of the prosthesis, embolization can occur where all or part of the neointima detaches and can become trapped in small blood vessels. The surface morphology, or surface topography, of the implant, has been shown to have a major effect on the adherence and development of the neointima lining.

Presently used techniques for forming the luminal surface of cardiovascular prostheses involves the use of woven or smooth synthetic materials. There is no control of uniformity in the blood contacting surfaces. A technique that allows for precise, tailor-made blood contacting surfaces would be of considerable value.

SUMMARY OF THE INVENTION

In accordance with one embodiment of the present invention, a synthetic blood vessel is provided, and a method for forming its internal surface is provided, wherein the internal surface has a closely-controlled microstructure which promotes the build up and firm attachment of a neointima lining thereto. A mold device against which the inner surface of the synthetic blood vessel is molded, includes a surface with microscopic upstanding pillars arranged in a predetermined pattern, with all pillars of a controlled geometry. The mold device can be formed of Teflon (polytetrafluoroethylene) using photolithographic processes, by sputter depositing onto the Teflon a material such as gold, which a photoresist can adhere to.

A photoresist is applied over the material on the Teflon and patterned to define the pillar locations. The patterned surface is then sputter etched using an ion beam resulting in the formation of upstanding pillars in areas protected by the photoresist.

The novel features of the invention are set forth with particularity in the appended claims. The invention will be best understood from the following description when read in conjunction with the accompanying drawings.

BRIEF DESCRIPTION OF THE DRAWINGS

FIG. 1 is a perspective view of a synthetic blood vessel constructed in accordance with the present invention.

FIG. 2 is a partial sectional view of the blood vessel of FIG. 1, showing the pattern of recesses in its inner surface.

FIG. 3 is a partial perspective view, showing the blood vessel of FIG. 1 as it can be molded on a mandrell of the present invention.

FIG. 4 is an enlarged perspective view of a portion of the mandrell of FIG. 3, showing the pattern of pillars on its molding surface.

FIGS. 5-9 are sectional views illustrating steps in the formation of the pattern of the mold device of FIG. 4.

FIG. 10 is a sectional view of an ion beam generator used in the process of FIG. 9.

DESCRIPTION OF THE PREFERRED EMBODIMENTS

FIG. 1 illustrates a synthetic blood vessel prostheses 10 of the present invention, which has tubular walls 12 that form an inner surface 14 that is to carry blood. The natural tendency of the blood is to try to incorporate the prostheses into the body by encapsulating it in living tissue. The attempt to encapsulate includes the deposition of various components of the blood onto the prostheses surface 14. If all goes well, a healthy neointima lining is formed on the surface 14. It is important that the neointima lining be securely anchored to the inner surface 14, so that it does not later become detached and block a downstream smaller blood vessel. As shown in FIG. 2, the inner surface 14 includes a large number of microscopic recesses 16 that each have a considerable depth with respect to their width, and which each have a substantially constant cross section along their depth. Components of blood can anchor themselves within the recesses 16 to prevent detachment of a built up lining. The recesses 16 must have a small width or diameter, in order that blood components can be anchored in it, but not too small or else blood components cannot easily flow into the recess. A diameter on the order of 10um (micrometers) is desirable. The sides of the recesses should be substantially perpendicular to the wall surface 14, to resist washing away of blood components. The depth of the recesses should not be too great compared to the thickness T of the blood vessel walls in order to avoid substantial weakening of the blood vessel walls. A recess depth about two to three times the recess width is desirable. It is highly desirable that the configuration and pattern of the recesses be easily controllable, so that a configuration and pattern that is found to be especially stable can be reproduced.

As shown in FIG. 3, the synthetic blood vessel 10 is constructed by molding it, and particularly its inner surface 14, on a mold device 18 such as a largely-cylindrical mandrel, which has a multiplicity of upstanding pillars 22 extending from the mold surface 20.

FIG. 4 illustrates a portion of the surface 20 of the mold device, showing one configuration of the upstanding pillars 22 and of their pattern. In one example, each pillar has a width of about 14um, a height H of about twice as much such as about 30 um, and has substantially the same hexagonal cross section along its entire height.

The mold device 18 is formed by a photolithographic process. In such a process, a layer of photoresist is applied to a mass of the mold material. A photomask, with the prescribed pattern, is placed in intimate contact with the photoresist on the mold material. Areas of the photoresist not covered by the pattern on the photomask are exposed to light. The photoresist is then developed leaving the prescribed pattern on the mold material. The mold with a pattern of photoresist is then ion etched to remove a depth of material except at the pillar areas, to leave pillars.

An ideal material for molding and for ion etching is Teflon (a trademark of duPont de Nemours for polytetrafluoroethylene). Such material has about the lowest surface energy of any material so that almost nothing sticks to it, which aids in removing the mold from a molded product. This is especially important where long thin pillars are to be molded. Teflon has an especially high ion beam etch rate, relative to other materials. It may be noted that the etching process increases the material surface energy by microscopically roughening the surface and generating dangling bonds in the polymer, but the surface energy is still relatively low. It would be possible to use a thin nickle mesh mask through which to ion etch. However, it is difficult to maintain such a mask in intimate contact with the substrate being etched since the nickle mesh masks are very difficult to handle. It was found that the masks cracked and wrinkled from handling. In areas where mask-substrate contact was poor, pattern resolution was lost and the mask degraded due to heat from etching.

A major problem with the use of Teflon is that it is very difficult to make a photoresist stick to the Teflon surface, because of the very low surface energy of Teflon. In accordance with one aspect of the present invention, applicant applies a layer of an intermediate material to the Teflon by energetically projecting submicroscopic particles of the intermediate material onto the Teflon surface to form a thin film. This can be accomplished by sputter depositing a metal with a high ion etch rate such as gold onto the Teflon surface. FIG. 5 illustrates a portion of the mold device 18A prior to the formation of pillars therein, with a thin layer 24 of metal such as gold applied to its surface 20A by sputter deposition.

A next step, shown in FIG. 6, is to apply a layer of photoresist 26 over the sputtered-on gold layer 24. Photoresist can be applied in a uniform layer by spinning the mold device with liquid photoresist on it, dipping the mold device in photoresist, or spraying on a layer of photoresist, using well-known methods. A next step, shown in FIG. 7, is to apply a photomask 30 lying facewise against the photoresist film 26, and to direct light, indicated at 31, through the mask to the photoresist. The light 31 is very well collimated to expose the photoresist with high definition. Either a positive or negative resist can be used, and a corresponding dark field or light field mask can be used. A particular mask 30 is shown as having opaque regions 32 where the pillars are to be formed, with the rest of the mask 33 being transparent. After the photoresist is exposed, it is subjected to a developing process which washes away all of the photoresist except those areas 26B that define the cross section of a pillar. The covered workpiece with pillar areas covered by photoresist areas 26B is shown in FIG. 8.

A next step, shown in FIG. 9, is to apply an energetic ion beam, indicated at 36, to etch the surface of the device so as to leave the upstanding pillars 22. The ion beam must be able to etch through the gold layer 24 and the desired depth of the mold material (such as Teflon) before it etches through the photoresist areas 26B and the gold layer under it in order to produce upstanding pillars. Afterwards the photoresist over each pillar can be dissolved as with acetone, and the gold dissolved by an acid. As discussed above, Teflon has a very high ion beam etch rate, which greatly facilitates formation of tall pillars. Teflon is also useful because of its high chemical inertness, which allows the removal of the photoresist 26B and the gold 24 without removal of appreciable amounts of the Teflon. It is possible to use other materials, for the mold device, although difficulties are anticipated. It may be noted that the interpillar space 40 of the mold device has a grass-like microstructure, which results from the ion beam sputtering. The Teflon mold device with the pillars therein, can be used to mold the inside surface of a small (under 6mm inside diameter) synthetic blood vessel in a number of ways such as by casting the synthetic blood vessel material around a mold device mandrel and either expanding the blood vessel (with pressured gas) or contacting the mandrel. It may be noted that a material named Biomer is a preferred material for synthetic blood vessels.

Applicant has formed microscopic pillars of the type shown in the drawings by the method described above. The surface 20A (FIG. 5) of the mold device 18A first had to be polished, to remove irregularities of the same order of magnitude as the pillars to be formed. The pillars preferably have a width no more than about 25 microns. Polishing was accomplished by smoothing the surface and finally polishing it with 0.5um diamond grit. During polishing, care was taken to maintain the mold surface flat, to assure that the mask later applied over the photoresist and gold would make good facewise contact with the photoresist.

The gold film 24 was applied by sputter depositing followed by an ultrasonic cleaning and a rinse with ethanol. Gold is especially useful because of its high sputter yield. In sputter depositing, an ion beam is directed at a quantity of material to be deposited, to knock out particles that are somewhat energetically deposited. Other materials that could be sputter deposited, and which have a high ion etch rate are copper, gold and palladium, and brass. The sputtered-on particles have just enough energy to penetrate the Teflon to a depth of a few molecules, to anchor themselves and provide a base for additional particles to build up a film on the Teflon. If very energetic particles (e.g., over 100 eV for most materials, or over 10 eV for Teflon) were applied, they would be implanted so deeply that they could not be removed without damaging the pillars. Particle energies of under 1 eV can readily build up securely onto Teflon. These particle energies are energetic compared to techniques of electroplating or spinning on materials where the particle energies are substantially zero (much less than 0.01 eV). In ion beam etching, energies of over 100 eV are applied, typically to an inert gas.

The thickness of the gold layer 24 is important, with a thickness of about 0.3um found to be satisfactory. If the gold film thickness is much less than that, such as less than about 0.15um, then during the exposure of photoresist (FIG. 7), light passes through the photoresist and the gold layer, and is diffused by the Teflon and causes a "wash out" or reduced resolution of the desired photoresist pattern created at 26B. The gold film 24 should not be too thick, since the sputter etch rate of gold is considerably less than that of Teflon, which increases the time for ion etching. Also, a thicker gold layer may be more uneven, which could allow some of the pillars to be partially etched away before the interpillar areas have been removed to the desired depth. Accordingly, it is preferred that the thickness of the gold film be less than 3 microns in thickness.

In some experiments, applicant has applied a positive resist, by applying Shipley Microposit, and has applied a negative photoresist by applying Kodak Micro Resist 752. It may be noted that both of these photoresists will either run off or bead upon a bare Teflon surface. These resists were chosen because they each have a very high resistance to ion etching. Layers of photoresist of these materials in a thickness of about 0.4um were applied over the gold. After ion beam etching through the 0.3um gold film and about 20um of Teflon, the thickness of the photoresist layers decreased from about 0.4um to about 0.15um.

The ion beam used to sputter etch the targets was generated by an argon ion source shown in FIG. 10. Argon gas was admitted to the source through a gas inlet 44 to the region of a cathode filament 46. An anode 48 was maintained at a potential of about 40 volts with respect to the cathode, to draw electrons from the cathode. A coil 50 applied a magnetic field of about 50 Gauss to increase the pathlength of the electrons, to thereby increase the plasmac density in a region behind a screen grid 50. The screen grid was a few tens of volts below the plasma potential to extract ions to form an ion beam. The ion beam was accelerated by an accelerator grid 52 maintained at a voltage between 1,000 and 2,000 volts with respect to the screen grid 50, to produce ion beam energies ranging from 1,000 to 2,000 eV, with beam current densities ranging from 0.25 to 0.7mA/cm$^2$ at the target. The Teflon was separated by about 15cm from the accelerator grid 52. The ion beam divergence angle was approximately 10°. The Teflon targets were rotated under the beam to minimize the effects of any ion beam non-uniformity. The ion beam was applied for about 15 minutes to produce pillars of a height of about 40um and width of about 14um, in a pattern containing about 64,500 pillars in an area of 6.5cm$^2$.

Thus, the invention provides a method and apparatus for producing a cardiovascular prostheses which has a multiplicity of microscopic blind holes on its luminal surface. A mold device is formed with multiple pillars, and the cardiovascular prostheses is molded or cast against the pillared surface to form a pattern of deep but blind holes in the prostheses into which blood particles can anchor themselves to form a neointima lining which will not break free. The pillars are formed by ion etching a Teflon mold device with the pillar areas protected by a photoresist that is highly resistant to ion etching (at least ten times as resistant as the Teflon workpiece) applied by lithographic methods. The photoresist is bonded to the Teflon surface by an easily sputter etched intermediate layer which was sputter deposited onto the Teflon surface.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for forming a device having a plurality of upstanding microscopic pillars, that is useful in forming a multiplicity of microscopic blind holes in a synthetic blood vessel or the like, comprising:
    energetically projecting a multiplicity of submicroscopic particles of a first material against a surface of an initial mold device of a second material to energetically deposit the particles onto the mold device surface and build up a thin film of the particles over the mold device surface;
    applying a layer of photoresist material over said first material, said first material being one to which said photoresist can be bonded more readily than to said second material;
    applying a mask to said photoresist layer, said mask having a pattern of opaque and light transmitting regions defining the locations and cross sections of said pillars, applying light through said mask to said photoresist, and removing areas of said photoresist around said locations, to form a pattern-covered mold device which includes separated locations of photoresist over said film;
    applying an ion etching beam to said pattern-covered mold device that readily etches both said first and second materials but not said photoresist, in an amount that removes said film of said first material and the mold device material under it in areas not covered by said photoresist, to thereby form microscopic pillars in said mold device surface.

2. The method described in claim 1 wherein:
    said second material is Teflon, whereby to facilitate the formation of pillars of large height to width ratio.

3. The method described in claim 2 wherein:
    said first material is gold, and the thickness of said gold first material is at least 0.15 but less than 3 microns, whereby to prevent dispersion of light by the underlying Teflon while permitting ion etching.

4. The method described in claim 1 wherein:
    said mold article surface is largely cylindrical; and including
    removing said photoresist and first material from said pillars;
    applying a moldable material to the outside surface of said mold article, in a thickness greater than the height of said pillars, and removing said mold article, whereby to enable production of article blood vessels all having a known pattern of blind recesses for anchoring bodily material thereto.

5. The method described in claim 1 wherein:
    each pillar has a width of no more than about 25 microns; and including
    forming said mold device surface flat and polishing said mold device surface with grit no more than about one micron diameter prior to said step of projecting particles against said mold device surface, and said step of applying a mask includes laying a flat mask in intimate facewise contact with said layer of photoresist material.

6. A method for use in forming apparatus that is useful in molding a synthetic blood vessel comprising:
    forming a smooth even surface on a workpiece of a mold material which is resistant to the adherence of photoresist material thereto:

sputter depositing a film of easily etched material onto said surface;

applying a film of photoresist material which is resistant to ion etching to said sputter deposited film, wherein said photoresist material adheres to said deposited film but not to said mold material;

applying a photo mask having a pattern of spaced dots to said film of photoresist, and directing light through said mask onto said photoresist;

removing said mask, and removing all areas of said photoresist except those which lay under said dots, to leave a covered workpiece covered by said deposited film and said dots of photoresist;

applying an ion etching beam to said covered workpiece which more readily etches the material of said mold and said sputter deposited film than said film of photoresist material, in an amount that removes said sputter-deposited film and a depth of said workpiece material but not all of the thickness of said dots of photoresist and the deposited film thereunder, to form a workpiece with a mold surface having upstanding pillars which is useful in molding the inner surface of a synthetic blood vessel.

7. The method described in claim 6 including:

casting a material against said mold surface, to a thickness greater than the height of said pillars, to form a synthetic blood vessel with a pattern of blind holes therein.

8. A method for forming a microscopic contoured surface in a surface of a Teflon workpiece, comprising:

sputter depositing a first material onto said surface of the Teflon workpiece to form a film of said first material thereon;

forming a film of photoresist over said film of first material, the material of said photoresist adhering more strongly to said first material than to Teflon;

directing light in a pattern onto said photoresist, and washing away portions of said photoresist corresponding to said pattern, to leave a covered workpiece;

applying an ion etching beam to said covered workpiece;

said photoresist film being more resistant to etching by said ion beam than said first material film or said Teflon.

9. The method described in claim 8 wherein:

said step of sputter depositing comprises directing particles of said first material at said workpiece with an energy of less than 10 eV, and said step of applying an ion etching beam includes applying ions of an inert gas with energies of over 100 eV.

* * * * *